US006902338B2

(12) United States Patent
Puvvada et al.

(10) Patent No.: US 6,902,338 B2
(45) Date of Patent: Jun. 7, 2005

(54) CUSTOMIZED PERSONAL CLEANSING ARTICLE

(75) Inventors: Sudhakar Puvvada, Shelton, CT (US); Thomas Morikis, Unionville, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 197 days.

(21) Appl. No.: 10/328,919

(22) Filed: Dec. 26, 2002

(65) Prior Publication Data

US 2004/0126177 A1 Jul. 1, 2004

(51) Int. Cl.[7] .......................... A47K 7/02; A61K 7/50

(52) U.S. Cl. .......................... 401/201; 510/141

(58) Field of Search .......................... 401/6, 196, 200, 401/201; 510/141, 146, 294

(56) References Cited

U.S. PATENT DOCUMENTS 14,710 A * 4/1856 Hobbs .......................... 42/60
1,682,119 A 8/1928 Field
1,791,359 A * 2/1931 Henriksen .......................... 510/146
2,607,940 A 8/1952 Miller
2,613,185 A * 10/1952 Marshall .......................... 510/146
3,167,805 A 2/1965 Zuppinger et al.
4,190,550 A 2/1980 Campbell
4,228,834 A 10/1980 Desnick
4,480,939 A 11/1984 Upton
4,789,262 A 12/1988 Sanchez
5,462,378 A 10/1995 Webb
5,839,842 A 11/1998 Wanat et al.
6,015,242 A 1/2000 Gillis
6,042,288 A 3/2000 Rattinger et al.
6,174,845 B1 * 1/2001 Rattinger et al. .......................... 510/146
6,211,129 B1 4/2001 Gladfelter et al.
6,461,069 B1 * 10/2002 Williams .......................... 401/201

FOREIGN PATENT DOCUMENTS

JP 10-137152 5/1998

OTHER PUBLICATIONS

*Int'l. Search Report No. PCT/EP 03/13640, dated Mar. 24, 2004, 2 pp.*

* cited by examiner

*Primary Examiner*—David J. Walczak
(74) *Attorney, Agent, or Firm*—Alan A. Bornstein

(57) ABSTRACT

A customized cleansing article provides the user with an assortment of one or more of skin cleansing, aesthetic, and skin benefit bars contained within a porous pouch. The toilet bars are characterized by a rigidity index greater than 0.2 Mpa at 25 C.

7 Claims, 2 Drawing Sheets

CUSTOMIZED PERSONAL CLEANSING ARTICLE

BACKGROUND OF THE INVENTION

1. Field of the Invention

The invention relates to a personal cleansing article and more specifically to a personal cleansing article wherein an assembly of one or more of skin cleansing, aesthetic, and skin benefit toilet bars are contained within the confines of a porous pouch.

2. The Related Art

Toilet bar skin cleaning properties are well known. An ideal bar composition not only cleans but provides a large quantity of lather and leaves the skin feeling comfortable. Consumers also desire to obtain toilet bars with good hardness, low mush, and that contain appealing aesthetic ingredients such as fragrances, optionally one or more other aesthetic ingredients and one or more skin benefit agents such as emollients for moisturizing and treating the skin according to individual preferences and needs. To accomplish this, a wide variety of additives have been suggested for inclusion in toilet bars. Some additives enhance the physical properties of the bar such as lather volume, hardness and wear rate. Other additives effect the aesthetic and sensory properties of the bar. Still other additives enhance skin moisturization, residual antibacterial properties, and treat skin conditions such as acne, etc. Unfortunately not all potentially desirable additives may be compatible with each other. As a result, a single toilet bar product is not suitable or desirable for every consumer. At the same time, the bar manufacturer desires to reduce costs by minimizing the difference in toilet bar compositions it produces.

The use of a porous or netted bag or pouch to carry soap is known. The prior art includes U.S. Pat. No. 1,682,119 where a bag is provided with soap in a flake or fragment form. Similarly U.S. Pat. No. 2,607,940 discloses a mesh bag so that a soap can be easily inserted. Similar arrangements are taught in e.g. U.S. Pat. No. 3,167,805, U.S. Pat. No. 4,190,550, U.S. Pat. No. 4,228,834, U.S. Pat. No. 4,48,0939, and U.S. Pat. No. 5,462,378. U.S. Pat. No. 4,789,262 teaches a soap holding cleaning pad. U.S. Pat. No. 5,839,842 discloses a cleansing system with a toilet bar and a sponge in a porous pouch. U.S. Pat. No. 6,042,288 teaches the use of a synthetic detergent bar and a pouf for holding the bar. JP Patent No. 10137152 also teaches a solid soap in an expansible net. The problem with prior art toilet bar and pouch implements is the inability to make available a product with a wide range of sensory properties in a convenient format but with excellent physical properties.

Surprisingly it has been found that when a single toilet bar is formulated with high levels of benefit agents such as a moisturizing agent, and aesthetic ingredients such as a fragrance, the wear rate and lather volume properties of the toilet bar such as lather, wear rate etc. are substantially degraded compared to a system of individual toilet bars formulated separately where a cleansing bar, a benefit agent bar, and an aesthetic agent bar are separately produced. For the purposes of this invention, a "bar" is herein defined as an individual toilet bar or other geometrically or amorphous shaped body that may be selected from and combined with other toilet bars or bodies according to the invention. According to the present invention, these separate bars may be combined in a porous pouch to bring together all the cleansing and skin treatment attributes desired by the consumer and at the same time form a useful cleansing implement with superior lathering properties compared to a single toilet bar formed with the same cleansing and skin treatment ingredients. Furthermore it has been found that production efficiency is enhanced by making the bars separately since such bars if made by the melt cast process have a shorter solidification time. Moreover the variability of solidification time in melt cast bars may be minimized by separate manufacturing of the bars. With respect to extrusion of such bars, the variability of processing parameters such as extrusion rate and stampability may also be minimized by separate manufacture of the bars.

SUMMARY OF THE INVENTION

In one aspect of the invention is a cleansing article, including:

a closable receptacle formed of a porous material;

a plurality of solid or semi-solid bars held in the receptacle including a first bar having a cleansing composition and a second bar having second composition selected from an aesthetic composition, a skin benefit composition or a combined aesthetic and benefit composition; wherein the cleansing and second compositions differ from each other; and wherein the cleansing composition contains a surfactant selected from a synthetic anionic surfactant, a soap, and a blend thereof in a concentration greater than about 5% by wt. (preferably greater than about 10% by wt.) and the second composition contains an aesthetic ingredient, a skin benefit ingredient or a blend thereof; the aesthetic or benefit ingredient being present in a concentration that is greater than the concentration of the same ingredient in the cleansing composition.

Preferred embodiments of the invention will now be described by way of example with reference to the accompanying drawings wherein like figures represent like features.

DETAILED DESCRIPTION OF THE INVENTION

The present invention consists of a cleansing article where 2 or more solid/semi-solid toilet bars are contained in a porous closable pouch. The toilet bars may serve different functions such as cleansing, benefit delivery etc. They may also have different ingredients that combine together to provide a unique benefit or fragrance. The compositions may also be inert and provide e.g. a massage or exfoliation type action and the like.

Advantageously the cleansing article contains a bar with an aesthetic ingredient that is selected from fragrances, colorants, pigments, cosmetics, suspended bodies and blends thereof; and a benefit ingredient that is selected from emollients, skin active materials and blends thereof. Preferably the aesthetic component is a combination of a fragrance and colorant. Preferably the first and second toilet bars of the cleansing article have a rigidity index greater than about 0.2 Mpa at 25 C.

Advantageously the cleansing article contains a toilet bar with a cleansing composition having about 15 to 80% by wt.

of a C8 to C24 acyl isethionate, or about 15 to 80% by wt. of a soap. More preferably the cleansing article contains at least one bar whose composition includes an amphoteric surfactant in combination with the anionic surfactant.

Advantageously the cleansing article contains a toilet bar with a benefit composition that includes an emollient selected from silicone oils and gums; fats; triglyceride oils; waxes; hydrophobic plant extracts; fatty esters, hydrocarbons and blends thereof. Preferably the benefit composition also includes a component selected from vitamins, antimicrobial agents, acne medications, exfoliating agents, astringents, antioxidants, enzymes, sunscreens and ultraviolet radiation absorbing compositions, and the like.

Preferred embodiments of the invention will now be described by way of example with reference to the accompanying drawings wherein like figures represent like features.

Figure 1:
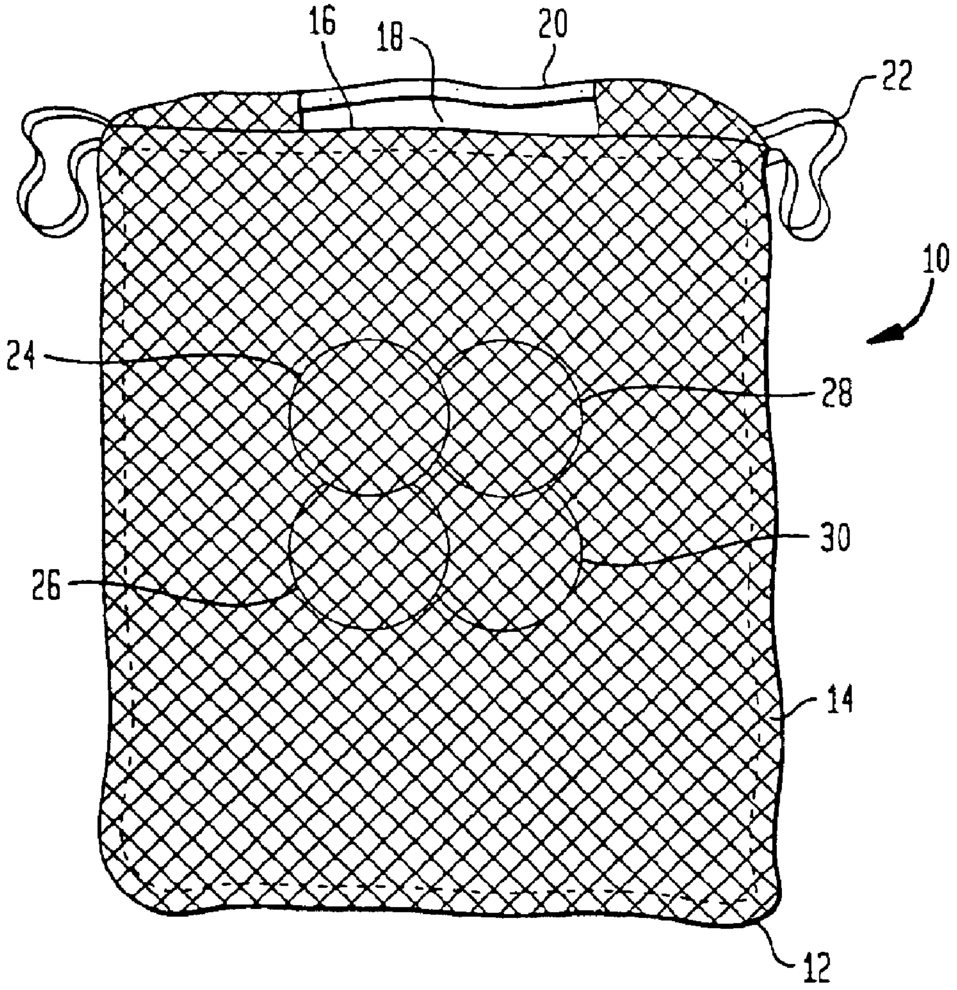
FIG. 1 is a perspective view of a preferred embodiment of the inventive cleansing implement, parts being broken away for clarity.
Figure 2:
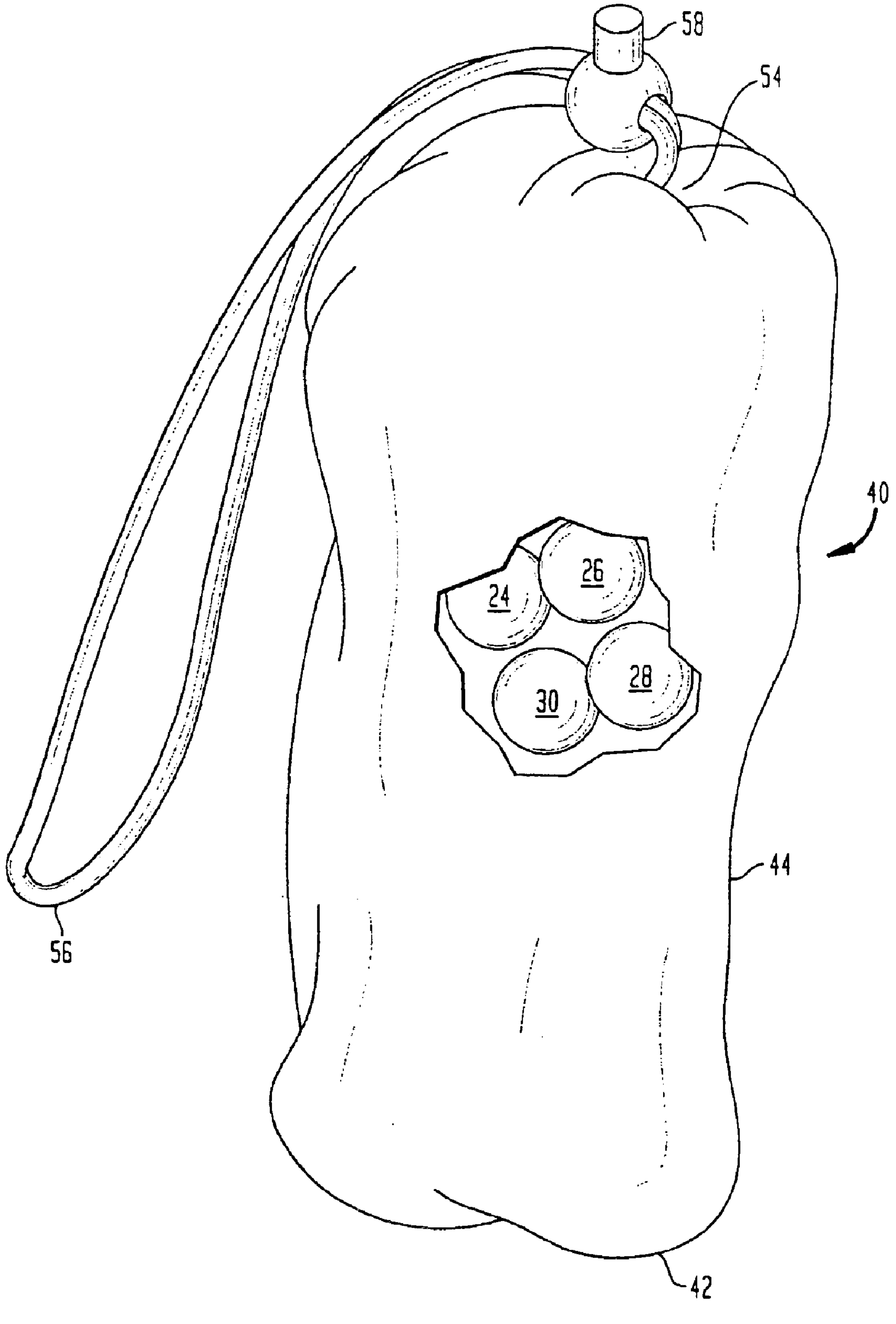
FIG. 2 is a perspective view of a second preferred embodiment of the inventive cleansing implement, parts being broken away for clarity.

A preferred embodiment of the inventive cleansing article is depicted in FIG. 1. The inventive cleansing article may be pre-assembled or preferably assembled by the user by inserting for example one or more of a cleansing bar 24, a aesthetic agent bar 26, a first benefit agent bar 28, and a second benefit agent bar 30 through opening 18 into the pocket 16 of bag holder 10. After all of the bars desired for the article have been inserted, pull ties 22 may be pulled that together with elastic band 20 and closed end 12 will serve to keep the bars inside the expandable mesh body 14 of the bag holder 10 until they are either exhausted or until such time as the user desires to use a new selection of bars. An alternative embodiment of the inventive cleansing article is depicted in FIG. 2. In similar fashion, the inventive cleansing article may be pre-assembled or preferably assembled by the user by inserting for example one or more of a cleansing bar 24, a aesthetic agent bar 26, a first benefit agent bar 28, and a second benefit agent bar 30 through opening 18 into the closable opening 54 of bag holder 40. After all of the bars desired for the article have been inserted, pull tie 56 may be pulled so that together with cord locking device 58 and closed end 42 will serve to keep the bars inside the porous fabric pouch 44 of the bag holder 40 until the bars are either exhausted or until such time as the user desires to replace one or more of the used bars with a new selection of bars.

Surfactants:

Surfactants are an essential ingredient of at least one of the toilet bars of the invention. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

Soaps

At least one of the toilet bars such as the cleansing bar, may contain soap, preferably it contains at least 0.1% by wt. of soap. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

Synthetic Anionic Surfactants

At least one of the toilet bars of the present invention may contain one or more non-soap anionic detergents. The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

$R^4O_2CCH_2CH(SO_3M)CO_2M$; and amide-MEA sulfosuccinates of the formula;

$R^4CONHCH_2CH_2O_2CCH_2CH(SO_3M)CO_2M$ wherein $R^4$ ranges from $C_8$–$C_{22}$ alkyl and M is a solubilizing cation.

Sarcosinates are generally indicated by the formula:

$R^1CON(CH_3)CH_2CO_2M$, wherein $R^1$ ranges from $C_8$–$C_{20}$ alkyl and M is a solubilizing cation.

Taurates are generally identified by formula:

$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

At least one of the toilet bars preferably contains non-soap anionic surfactants, preferably $C_8$–$C_{14}$ acyl isethionates. These esters are prepared by reaction between alkali metal isethionate with mixed aliphatic fatty acids having from 6 to 12 carbon atoms and an iodine value of less than 20.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

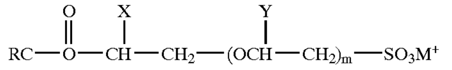

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In another embodiment of at least one of the toilet bars in the inventive cleansing article, e.g. the aesthetic agent bar, or benefit agent bar, there is less than 25% by wt. of anionic surfactants: Preferably there is less than 20%, and more preferably less than 15% by wt. of these surfactants.

Anionic surfactants may be usefully employed in the cleansing bar of the present invention in the concentration range of about 5 to 90% by wt., preferably in the concentration range of about 20 to 60% by wt.

Amphoteric Surfactants

One or more amphoteric surfactants may be used in at least one bar of this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

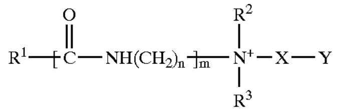

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

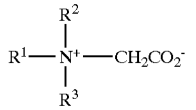

and amido betaines of formula:

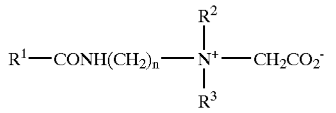

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

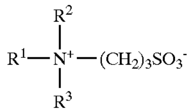

or

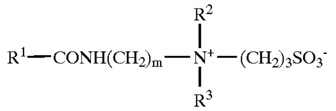

where m is 2 or 3, or variants of these in which $—(CH_2)_3SO_3^-$ is replaced by

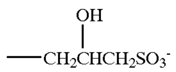

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Zwitterionic and/or amphoteric surfactants may be usefully employed in the cleansing bar of the present invention in the concentration range of about 0 to 30% by wt., preferably in the concentration range of about 1 to 20% by wt.

Nonionic Surfactants

One or more nonionic surfactants may also be used in at least one of the cleansing bars of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Nonionic surfactants may be usefully employed in the cleansing bar of the present invention in the concentration range of about 0 to 30% by wt., preferably in the concentration range of about 1 to 20% by wt.

Cationic Surfactants

One or more cationic surfactants may also be used in the inventive toilet bar composition.

Examples of cationic detergents are the quaternary ammonium compounds such as alkyldimethylammonium halogenides.

Cationic surfactants may be usefully employed in the cleansing bar of the present invention in the concentration range of about 0 to 30% by wt., preferably in the concentration range of about 1 to 20% by wt.

Other suitable surfactants which may be used are described in U.S. Pat. No. 3,723,325 to Parran Jr. titled "Detergent Compositions Containing Particle Deposition Enhancing Agents" issued March, 27, 1973; and "Surface Active Agents and Detergents" (Vol. I & II) by Schwartz, Perry & Berch, both of which are also incorporated into the subject application by reference.

Aesthetic Agents:

In addition, at least one of the bar compositions may be an aesthetic agent bar and may include fragrances, colorants, pigments, particles, suspended materials, blends thereof, and the like. When they are employed, fragrances are advantageously used in the range of about 0.1 to 10% by wt., colorants in the range of about 0.000001 to 1% by wt., and particles/suspended materials in the range of about 0.01 to 10% by wt.

Preferably the bars employed in the inventive article may be differentiated from each other by different colorants where the color signifies a specific attribute to be conferred by the bar or where color is used as a descriptor of the bar.

Benefit Agents

Benefit Agents:

The personal cleansing article of the present invention may contain toilet bar compositions that contain a safe and effective amount of a benefit agent. This benefit agent may be selected from water-soluble active agents, oil soluble active agents, pharmaceutically acceptable salts and mixtures thereof. The term "benefit agent" as used herein means personal care actives that can be used to deliver a benefit to the skin and/or hair. The term "safe and effective amount" as used herein, means an amount of benefit agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the benefit agents described herein. What is a safe and effective amount of the active agent ingredient will vary with the specific active agent, the ability of the active to penetrate through the skin, the age, health condition, and skin condition of the user, and other like factors. Preferably the benefit agent containing toilet bars of the present invention comprise from about 0.01% to about 50%, more preferably from about 0.05% to about 25%, even more preferably 0.1% to about 10%, and most preferably 0.1% % to about 5%, by weight of the benefit agent component.

A wide variety of benefit agent ingredients are useful herein and include those selected from emollients, anti-acne actives, anti-wrinkle and anti-skin atrophy actives, skin barrier repair aids, cosmetic soothing aids, topical anesthetics, artificial tanning agents and accelerators, skin lightening actives, antimicrobial and antifungal actives, sunscreen actives, sebum stimulators, sebum inhibitors, anti-glycation actives and mixtures thereof and the like.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives thereof, and the like. Antimicrobial and antifungal actives can be effective to prevent the proliferation and growth of bacteria and fungi. Nonlimiting examples of antimicrobial and antifungal actives include antibiotic drugs, quaternary ammonium compounds such as benzalkonium chloride; benzethonium chloride; triclosan; triclocarban; and mixtures thereof and the like. Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include retinoic acid and its derivatives, and the like. Skin barrier repair actives are those skin care actives which can help repair and replenish the natural moisture barrier function of the epidermis. Nonlimiting examples of skin barrier repair actives Ceramide derivatives; mixtures thereof, and the like. Non-steroidal Cosmetic Soothing Actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include diphenhydramine and the like. Artificial tanning actives can help in simulating a natural suntan by increasing melanin in the skin or by producing the appearance of increased melanin in the skin. Nonlimiting examples of artificial tanning agents and accelerators include dihydroxyacetone and the like. Skin lightening actives can actually decrease the amount of melanin in the skin or provide an such an effect by other mechanisms. Nonlimiting examples of skin lightening actives useful herein include phenolic and resourcinol derivatives, hydroquinone, and the like. Also useful herein are sunscreen actives. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, oxybenzone, and the like. Sebum stimulators can increase the production of sebum by the sebaceous glands. Nonlimiting examples of sebum stimulating actives include dehydroetiandrosterone (DHEA) and the like. Sebum inhibitors can decrease the production of sebum by the sebaceous glands. Nonlimiting examples of useful sebum inhibiting actives include aluminium hydroxy chloride salts and the like. Also useful as actives in the present invention are protease inhibitors. The protease inhibitors suitable for use in the present invention include, but are not limited to, proteinases such as serine proteases and peptidases, such as carboxypepidases, and the like. Other useful benefit ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and, and the like. Benefit agents in the present invention may also include anti-itch ingredients. Suitable examples of anti-itch ingredients which are useful in the compositions of the present invention include hydrocortisone, and the like. Suitable benefit agents may also include hair growth inhibitors, desquamating enzyme enhancers, and the like.

Optional Ingredients

In addition, the inventive cleansing article includes toilet bar compositions that may include 0 to 15% by wt. optional ingredients as follows:

sequestering agents, such as tetrasodium ethylenediaminetetraacetate (EDTA), EHDP or mixtures in an amount of 0.01 to 1%, preferably 0.01 to 0.05%; opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Emollients

As discussed above emollients may be advantageously used in the present invention as benefit agents. The emollient "composition" may be a single benefit agent compound or it may be a mixture of two or more compounds one or all of which may have a beneficial aspect. In addition, the benefit agent itself may act as a carrier for other compounds one may wish to add to one or more of the inventive toilet bars.

Humectants such as polyhydric alcohols, e.g. glycerine and propylene glycol, and the like; and polyols such as the polyethylene glycols listed below, and the like may be used as emollients or moisturizers.

| | |
|---|---|
| Polyox WSR-205 | PEG 14M, |
| Polyox WSR-N-60K | PEG 45M, or |
| Polyox WSR-N-750 | PEG 7M. |

Humectants may be usefully employed in at least one bar of the present invention in the concentration range of about 1 to 40% by wt., preferably in the concentration range of about 5 to 30% by wt.

Hydrophobic emollients, hydrophilic emollients, or a blend thereof may be used. Preferably, hydrophobic emollients are used in excess of hydrophilic emollients in at least one of the toilet bars. Most preferably one or more hydrophobic emollients are used alone. Hydrophobic emollients are preferably present in a concentration greater than about 0.5% by weight, more preferably about 4% by weight in at least one of the bars. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnuba, spermaceti, beeswax, lanolin, and derivatives thereof;

(d) hydrophobic and hydrophillic plant extracts;

(e) hydrocarbons such as liquid paraffins, Vaseline®, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins, minerals, and skin nutrients such as milk, vitamins A, E, and K; vitamin alkyl esters, including vitamin C alkyl esters; magnesium, calcium, copper, zinc and other metallic components;

(l) phospholipids;

(m) antiaging compounds such as alpha hydroxy acids, beta hydroxy acids; and (o) mixtures of any of the foregoing components, and the like.

Preferred emollient benefit agents are selected from C12 to C18 fatty acids, triglyceride oils, mineral oils, petrolatum, and mixtures thereof.

Emollients may be usefully employed in at least one bar of the present invention in the concentration range of about 1 to 90% by wt., preferably in the concentration range of about 10 to 60% by wt.

Structurants:

Solid structuring aids and fillers are advantageously used to maintain bar structural integrity. Examples of structuring aids include, but are not limited to polyalkylene glycols having MW of 2,500 to 10,000 and a melting point of about 40° C. to 65° C.; C8 to C20 alkanols, preferably straight chain, and saturated C14 to $C_{18}$ alkanols; C8 to C25 fatty acids; preferably straight chain, and saturated C14 to C22 fatty acids; and water soluble starches, such as maltodextrin and the like. The structuring aids and fillers generally comprise about 0 to 35% by weight of the bar composition, preferably about 10 to 25% by weight.

Pouch Materials:

The pouch may be formed of any porous or water permeable material sufficiently permeable to let water pass through the pouch and transfer the contents of the toilet bars that are either dissolved, dispersed, or suspended in the water to the user. Preferably the pouch material is sufficiently water insoluble so that maintains its integrity until the toilet bars are substantially used up. Useful materials include polymeric mesh, woven or nonwoven fabric, paper, tissue, sponge or laminate of foam and fabric. Advantageously a light weight polymeric meshed substrate may be used. A useful material is an extruded tubular netting mesh, particularly prepared from polyolefins such as polyethylene and the like, and other materials such as polyamides or polyesters and the like. They may be single or multiple ply netting such as in a pouf. The mesh structure may be polygonal, such as diamond shaped, or the like. Also suitable are irregular shapes. Advantageously the pouch cells are open and that preferably the contents within the pouch are observable from the exterior.

Optionally sponge like materials may also be included in the pouch. Useful sponge materials are closed cell materials either of synthetic or natural origin. Synthetic sponges are advantageously formed of foamed polyurethane and the like. Optionally the sponge material may be shaped to resemble an aesthetic form or be adapted to hold one or more of the toilet bars.

Examples of suitable nonwoven substrates useful as pouch materials would be wet-laid, dry-laid, spun bonded, hydroentangled, air-laid, and the like comprising either singly or in admixture fibers such as cellulose, rayon, polyester, polypropylene, polyethylene, polyamide, and the like. The term substrate also includes naturally occurring materials such as animal skin e.g. chamois leathers and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful as a pouch material in the present invention are silk fibers, keratin fibers and cellulosic fibers. Non-limiting examples of keratin fibers include those selected from wool fibers, camel hair fibers, and the like. Non-limiting examples of cellulosic fibers include those selected from wood pulp fibers, cotton fibers, hemp fibers, jute fibers, flax fibers, and mixtures thereof.

Non-limiting examples of synthetic materials useful as components in the present invention include those selected from acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orion®; cellulose ester fibers such as cellulose acetate, Arnel®, and Acele®; polyamides such as Nylons (e.g., Nylon 6, Nylon 66, Nylon 610 and the like; polyesters such as Fortrel®), Kodel®, and the polyethylene terephthalate fibers, Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers. Substrates made from natural materials useful in the present invention can be obtained from a wide variety of commercial sources.

Suitable pouch materials may include at least one apertured fabric, where a pattern is created by a network of bundled fiber segments surrounding apertures or holes; or in a contiguous nonwoven web which has been apertured or provided with slits or other openings. In one preferred embodiment, the water insoluble matterial is a substantially contiguous network of water insoluble fibers having a plurality of macroscopic openings. A macroscopic opening is defined as an opening that is large relative to the intrinsic pore size of the water insoluble material.

In a typical spunbond or bonded carded web, for example, a macroscopic opening would appear to the eye to be a deliberately introduced hole or void in the web rather than a characteristic pore between adjacent fibers, and specifically could have a characteristic width or major axis diameter of about 0.1 mm to about 10 mm, or larger; preferably about 1 mm to about 5 mm. A useful characteristic width may be defined as 4 times the area of the aperture divided by the perimeter. Useful fabric aperture densities are about 10 to 700 per square inch, preferably about 20 to 500 per square inch.

As discussed above, the nonwoven web may be made from synthetic fibers, as is known in the art, and may be a spunbond web, a meltblown web, a bonded carded web, or other fibrous nonwoven structures known in the art. For example, a polyester nonwoven web such as a low basis weight spunbond material could be provided with apertures through pin aperturing; perf embossing and mechanical stretching of the web; die punching or stamping to provide apertures or holes in the web; hydroentangling to impart apertures by rearrangement of the fibers due to the interaction of water jets with the fibrous web as it resides on a patterned, textured or three-dimensional substrate that imparts a pattern to the web; water knives that cut out desired apertures or holes in the web; laser cutters that cut out portions of the web; patterned forming techniques, such as air laying of synthetic fibers on a patterned substrate to impart macroscopic openings; needle punching with sets of barbed needles to engage and displace fibers; and other methods known in the art. Preferably, the openings are provided in a regular pattern over at least a portion of the pouch.

The pouch of the present invention can comprise two or more portions, each having a different texture and abrasiveness. The differing textures can result from the use of different combinations of materials or from the use of a substrate having a more abrasive side for exfoliation and a softer, absorbent side for gentle cleansing. In addition, separate portions of the pouch can be manufactured to have different permanent colors thereby helping the user to further distinguish the surfaces.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

EXAMPLE 1

Solidification Time and Wear Rate of Toilet Bars

The solidification time properties and wear rate of inventive toilet bars formulated according to tables 1 to 3 (compositions 1 to 3) and a comparative bars formulated by combining compositions 1, 2 and 3 in equal parts were assessed and the results are illustrated in table 8. The solidification time was measured until the bar could be removed from the bar mold with no sticking when kept at a temperature of −13 C. Wear rates were measured according to the procedure described below.

It was observed that that the inventive toilet bars, where the cleansing and benefit compositions are kept separate, had substantially shorter solidification times and lower wear rates compared to the comparative toilet bars where the compositions are combined together.

TABLE 1

Cleansing Composition 1

| Component | Wt. % |
|---|---|
| Sodium Cocoyl Isethionate | 30.7 |
| Coconut Acid | 3.8 |
| Stearic Acid | 4.6 |
| Sodium Isethionate | 1.1 |
| Lauryl Alcohol | 5.0 |
| Titanium Dioxide | 1.0 |
| EHDP | 0.02 |
| EDTA | 0.02 |
| Fragrance | 1.0 |
| Mineral Oil | 3.0 |
| Glycerin | 5.0 |
| 12 Hydroxystearic Acid | 19.8 |
| Sodium Lauryl Ether Sulfate | 8.0 |
| Alpha Olefin Sulfonate | 9.0 |
| Propylene Glycol | 5.0 |
| Water | 2.96 |
| Total | 100 |

TABLE 2

Benefit Composition 2

| Component | Wt. % |
|---|---|
| Sodium Cocoyl Isethionate | 23.0 |
| Coconut Acid | 2.8 |
| Stearic Acid | 3.4 |
| Sodium Isethionate | 0.9 |
| Lauryl Alcohol | 5.0 |
| Titanium Dioxide | 1.0 |
| EHDP | 0.02 |
| EDTA | 0.02 |
| Fragrance | 1.0 |
| Mineral Oil | 24.0 |
| Glycerin | 4.0 |
| 12 Hydroxystearic Acid | 13.0 |
| Sodium Lauryl Ether Sulfate | 7.3 |
| Alpha Olefin Sulfonate | 7.3 |
| Propylene Glycol | 4.0 |
| Water | 3.26 |
| Total | 100 |

TABLE 3

Cleansing/Aesthetic composition 3

| Component | Wt. % |
|---|---|
| Sodium Tallowate | 23.6 |
| Sodium Cocoate | 5.2 |
| Sucrose | 19.0 |
| Triethanolamine | 5.6 |
| Propylene Glycol | 16.9 |
| Water | 28.7 |
| Fragrance | 1.00 |
| Total | 100 |

EXAMPLE 2

An example of a toilet bar with a high level of fragrance suitable for use in the present invention is given in Table 4.

TABLE 4

Aesthetic composition 4

| Component | Wt. % |
|---|---|
| Sodium Tallowate | 22.7 |
| Sodium Cocoate | 5.0 |
| Sucrose | 18.3 |
| Triethanolamine | 5.4 |
| Propylene Glycol | 16.3 |
| Water | 27.3 |
| Fragrance | 5.00 |
| Total | 100 |

TABLE 5

Comparative Composition 5 (obtained by combining compositions 1, 2 & 3 in equal parts)

| Component | Wt. % |
|---|---|
| Sodium Cocoyl Isethionate | 17.9 |
| Coconut Acid | 3.3 |
| Stearic Acid | 2.7 |
| Sodium Isethionate | 0.7 |
| Lauryl Alcohol | 3.3 |
| Titanium Dioxide | 0.7 |
| EHDP | 0.015 |
| EDTA | 0.015 |
| Fragrance | 1.0 |
| Mineral Oil | 9.0 |
| Glycerin | 3.0 |
| 12 Hydroxystearic Acid | 11.0 |
| Sodium Lauryl Ether Sulfate | 5.1 |
| Alpha Olefin Sulfonate | 5.4 |
| Propylene Glycol | 8.1 |
| Water | 10.87 |
| Sodium Tallowate | 7.9 |
| Sodium Cocoate | 1.7 |
| Sucrose | 6.4 |
| Triethanolamine | 1.9 |
| Total | 100 |

TABLE 6

Benefit Composition 6

| Component | Wt. % |
|---|---|
| Stearic Acid | 75 |
| Mineral Oil | 25 |
| Total | 100 |

TABLE 7

Benefit composition 7

| Component | Wt. % |
|---|---|
| Sodium Tallowate | 17.6 |
| Sodium Cocoate | 3.9 |
| Sucrose | 14.3 |
| Triethanolamine | 4.3 |
| Propylene Glycol | 12.7 |
| Water | 21.4 |
| Mineral Oil | 24.8 |
| Fragrance | 1.00 |
| Total | 100 |

TABLE 8

Solidification times and wear rate results.

| Bar | Solidification time (min) | Pour temperature (C.) | Wear Rate g/wash | Texture of Finished Product |
|---|---|---|---|---|
| Cleansing Composition 1 (inventive) | 35 | 97 C. | 1.625 | Held together well, solid |
| Benefit Composition 2 (inventive) | 35 | 90 C. | 2.429 | Held together well, solid |
| Cleansing/Aesthetic Composition 3 (inventive) | 35 | 90.5 C. | 2.436 | Held together well, solid |
| Composition 5 (comparative, obtained by combining compositions 1, 2 & 3 in equal parts) | 55 | 93.3 C. | 4.391 | Very Soft, Mushy |

EXAMPLE 3

Lather Volumes

The lather volumes of bars A & B as described below were assessed as separate individual bars in the pouch and compared with bars A & B blended together in a 1:1 ratio as a single formulated bar in a similar pouch. The results are illustrated in table 9. Lather volumes were measured according to the technique described below. It was observed that that the inventive article containing separate toilet bars A & B had substantially greater lather volumes compared to the comparative toilet bar where the A & B formulation was combined into a single toilet bar.

TABLE 9

Lather Volume Data

| Toilet bar | Lather Volume (mls) | |
|---|---|---|
| | Bars A & B Separated in the pouch as individual bars (Inventive case) | Bars A and B combined in one formula and employed as 2 bars in the pouch (Comparative case) |
| Bar A = Cleansing Composition 1 Bar B = Benefit Composition 6 | 93.8 | 56.7 |
| Bar A = Cleansing/Aesthetic Composition 3 Bar B = Benefit Composition 6 | 80 | 0 |
| Bar A = Cleansing/Aesthetic Composition 3 Bar B = Benefit Composition 7 | 80 | 0 |

Method of Bar Production:

The bar compositions used in the examples herein were formulated using the following process. All materials were added to a mixer, heated to 94 C, mixed until all material dissolved completely and then poured into plastic molds. The molds were then cooled until the material had solidified and then were removed from the plastic mold.

DESCRIPTION OF TEST METHODS

Rigidity Index.

Equipment Used: Instron

Basic Method:

1. Load Cell with the solid/semi-solid bar that is equilibrated and maintained at a constant temperature of 25 C using a water bath.
2. Apply force from the top so that the solid/semi-solid bar is displaced at a rate of 10 mm/min through an orifice at the bottom of cell and measure the force applied in kN. The orifice has a diameter of 2 mm and a length of 60 mm.

The Pressure drop across the capillary length defines how rigid the material is. This rigidity index is defined as:

Rigidity Index=Pressure drop (kPA)=Force (kN)/Area (m^2)

Where the Area=PI*Diam^2/4

Diam=diameter of the rod applying the force, in this case 31.4 mm.

Wear Rate Measurement Procedure:

Procedure:

1. Weigh each bar to 0.01 gms, then place the bar in a soap dish.
2. Adjust tap water to 40 C, and keep running water into a bucket.
3. Immerse bar and hands in 40 C water in a bucket.
4. Remove bar and rotate 20 times (180° rotation for each time).
5. Repeat steps 3 and 4.
6. Immerse the bar for the third time and replace in the soap dish.
7. Add 7.5 ml of tap water to the soap dish at 25 C.
8. Repeat the wash procedure (steps 2–6) three more times during the first day of the test. Washings are done 2 hours apart.
9. After the last wash of the day, add 7.5 ml tap water at 25 C to the soap dish and let the bars sit overnight.
10. After 17 hours repeat wash procedure (steps 2–6) but this time place the bars on a drying rack under ambient conditions.
11. After 17 hours weigh the bars to 0.01 g.

Wear rate (g/wash)=Initial Wt (g)−Final Wt. (g)/5

Lather Volume Measurement Procedure:

Apparatus

Two large sinks and a measuring funnel are used. The measuring funnel is fabricated using a 10.5-inch diameter plastic funnel and a 300 ml graduated cylinder with the bottom cleanly removed. The cylinder is fitted with the 0 ml mark over the funnel stem. The cylinder is sealed onto the funnel.

Procedure a) Place the funnel at the bottom of the Sink #1. Add tap water to the sink until the 0 ml mark of the funnel is reached.

b) Generate lather.

1) Run tap on sink #2.
2) Adjust the temperature of the water to 30 C.
3) Holding the pouch with the bars between both hands under running water, rotate for 10 half turns (180 degrees/half turn).
4) Remove hands and pouch from under the running water.

5) Rotate the pouch 15 half turns (180 degrees/half turn).

6) Place funnel over hands and pouch.

7) Lower hands and funnel into Sink #1.

8) When hands and pouch are fully immersed, slide from under the funnel.

9) Lower funnel to the bottom of the sink.

10) Read the lather volume.

11) Remove the funnel from Sink #1.

12) Rinse funnel and hands in sink #2.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A cleansing article, comprising:

a. a closable receptacle formed of a porous material;

b. a plurality of solid or semi-solid bars held in the receptacle including a first bar having a cleansing composition and a second bar having second composition selected from an aesthetic composition, a skin benefit composition or a combined aesthetic and benefit composition; wherein the cleansing and second compositions differ from each other and c. wherein the cleansing composition contains a surfactant selected from a synthetic anionic surfactant, a soap, or a blend thereof in a concentration greater than about 5% by wt. and the second composition contains an aesthetic ingredient, a skin benefit ingredient or a blend thereof; the aesthetic or benefit ingredient being present in a concentration that is greater than the concentration of an aesthetic or benefit ingredient in the cleansing composition.

2. The cleansing article of claim 1 wherein the aesthetic ingredient is selected from fragrances, colorants, pigments, cosmetics, suspended bodies and blends thereof; and the benefit ingredient is selected from emollients, skin active materials and blends thereof.

3. The cleansing article of claim 1 wherein said first and second bars have a rigidity index greater than about 0.2 Mpa at 25 C.

4. The cleansing article of claim 1 wherein the cleansing composition further comprises an amphoteric surfactant.

5. The cleansing article of claim 1 wherein the cleansing composition comprises about 15 to 80% by wt. of a C8 to C24 acyl isethionate, or about 15 to 80% by wt. of a soap.

6. The cleansing article of claim 1 wherein the benefit composition includes an emollient selected from silicone oils and gums; fats; triglyceride oils; waxes; hydrophobic plant extracts; fatty esters, hydrocarbons and blends thereof.

7. The cleansing article of claim 1 wherein the benefit composition includes a component selected from vitamins, antimicrobial agents, acne medications, exfoliating agents, astringents, antioxidants, enzymes, sunscreens and ultraviolet radiation absorbing compositions.

* * * * *